United States Patent [19]

Stiles

[11] Patent Number: 5,118,295

[45] Date of Patent: Jun. 2, 1992

[54] DENTAL POST

[76] Inventor: Marlind H. Stiles, 3308 State St., Erie, Pa. 16508

[21] Appl. No.: 642,454

[22] Filed: Jan. 17, 1991

[51] Int. Cl.$^5$ .............................................. A61C 5/08
[52] U.S. Cl. ..................................... 433/221; 433/220
[58] Field of Search ................ 433/220, 221, 173, 174, 433/175

[56] References Cited

U.S. PATENT DOCUMENTS

| 224,355 | 2/1880 | Richmond | 433/221 |
| 635,773 | 10/1899 | Hamilton . | |
| 1,277,245 | 8/1918 | Murdock . | |
| 1,899,718 | 2/1933 | Poston . | |
| 2,866,285 | 12/1958 | Gerber . | |
| 3,548,499 | 12/1970 | Valen | 32/6 |
| 3,629,943 | 12/1971 | Gindea | 32/13 |
| 3,747,215 | 7/1973 | Joyner, Jr. | 32/13 |
| 4,203,217 | 5/1980 | Kurer | 433/220 |
| 4,239,489 | 12/1980 | Ellman et al. | 433/220 |
| 4,348,183 | 9/1982 | Weissman | 433/221 |
| 4,362,511 | 12/1982 | Jacklich | 433/220 |
| 4,427,383 | 1/1984 | Goldman | 433/220 |
| 4,600,391 | 7/1986 | Jacob | 433/220 |
| 4,645,457 | 2/1987 | Goldman et al. | 433/220 |
| 4,850,873 | 7/1989 | Lazzara et al. | 433/220 |
| 4,906,191 | 3/1990 | Soderberg | 433/213 |
| 4,995,810 | 2/1991 | Soderberg | 433/174 |

FOREIGN PATENT DOCUMENTS 3531389 3/1987 Fed. Rep. of Germany ...... 433/173

Primary Examiner—John G. Weiss
Assistant Examiner—Nicholas D. Lucchesi
Attorney, Agent, or Firm—Lovercheck and Lovercheck

[57] ABSTRACT

A method of installing a dental bridge in the mouth of a person who has lost several natural teeth leaving a space between his existing natural teeth with a viable root structure in the space. The method includes installing an implant adjacent each of the natural teeth, installing a post in the viable root structure and supporting the dental bridge on the post and on the two spaced implants, thereby using the viable root structure as a partial support for the bridge.

7 Claims, 2 Drawing Sheets

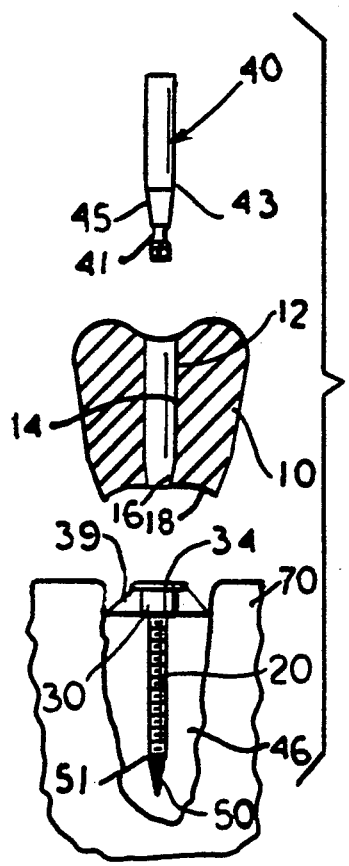
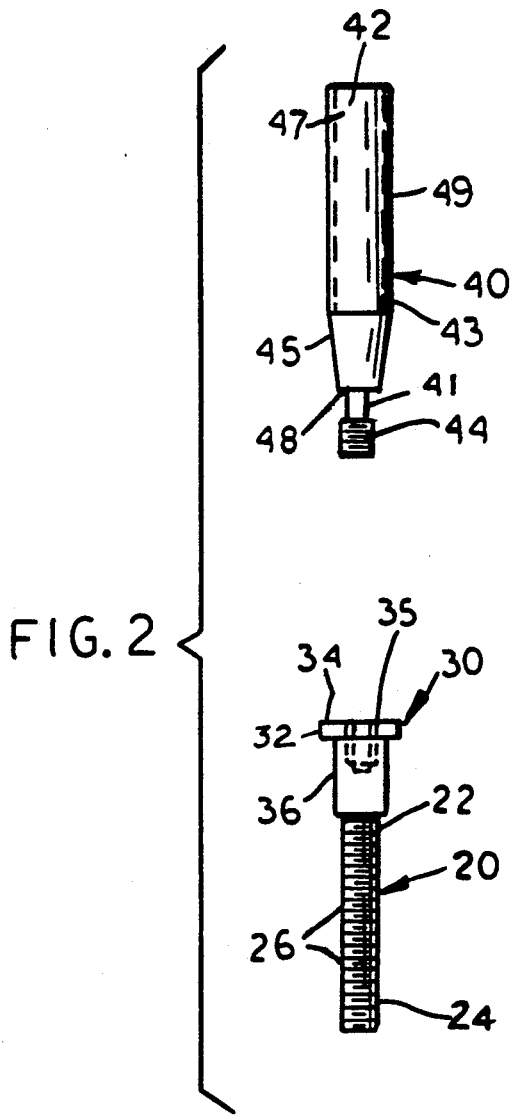
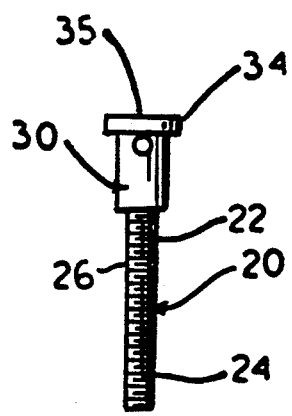
FIG. 3

DENTAL POST

BACKGROUND OF THE INVENTION

The present invention relates generally to dental prosthesis and more particularly to an improved device for removably attaching dental prosthesis to natural teeth as well as to implants and an improved method for installing dental prosthesis in the mouth of a person.

Applicant is aware of the following U.S. Pat. Nos: 635,773 to Hamilton; 1,277,245 to Murdock; 1,899,718 to Poston; 2,866,285 to Gerber; 3,548,499 to Valen; 3,629,943 to Gindea; 3,747,215 to Joyner, Jr.; 4,203,217 to Kurer; 4,239,489 to Ellman et al; 4,348,183 to Weissman; 4,362,511 to Jacklich; 4,427,383 to Galdman; 4,600,391 to Jacob; 4,645,457 to Goldman et al; 4,850,873 to Lazzara et al and 4,906,191 to Soderberg.

None of these patents show a structure for using a dental post for removably attaching a crown to a natural tooth, or removably attaching a bridge to two spaced natural teeth or to removably attach a bridge to an implant and to a natural tooth.

A dental post is used as an anchoring means for fixing a dental prosthesis when other fixing possibilities are lacking. Building up a dental prosthesis with anchoring means presently available is initiated by the insertion of a post into natural root structure retained on the jaw bone. Implant Dentistry made the removable prosthesis possible because of metal contacting metal. The device according to this invention allows this same concept to be applied to a natural tooth. Prior to Implant Dentistry, all fixed prosthesis were cemented in place and were likely to be destroyed in the removal process.

SUMMARY OF INVENTION

The present invention relates in general to the field of prosthodontic restoration, and more particularly to the combination of either a crown or a bridge with a post in a natural tooth root or any combination of the device with means for enabling a dentist to utilize an existing support to provide an improved support structure for a dental prosthesis.

In the case of one or more adjacent lost teeth, it is common practice to provide a bridge and to support the bridge on either an implant, a full natural tooth or a combination of both if available, or to support the bridge on natural teeth, as shown in U.S. Pat. No. 3,881,251 to Valen or to support the bridge on two adjacent implants.

The dental post disclosed herein will allow the following: (1) the bridge work to be attached and removed from natural tooth structure in the same fashion that the bridgework would be attached and removed from implants; (2) the dental post will allow for the attachment of bridgework to a natural tooth and an implant abutment or retainer and likewise its removal; (3) the dental post will update natural tooth technology to a par with implant prosthetic technology; (4) the post can be used as a single tooth crown retainer, bridge retainer or any of the various prosthetic retentive devices; and, (5) this post would also allow for removal of the prosthetic devices which would otherwise be permanently cemented in place.

It is an object of the invention to provide a dental prosthesis supported in a post in a natural tooth root either singularly or in conjunction with an implant.

Another object of the invention is to provide an improved support arrangement for a dental prosthesis.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

BRIEF DESCRIPTION OF THE DRAWING

FIG. 1 is an exploded view of a crown, post and retainer device to be applied to a natural tooth according to the invention.

FIG. 2 is an exploded view of a support structure according to the invention, for a dental prosthesis.

FIG. 3 is a side view of a dental post and super structure according to the invention.

DETAILED DESCRIPTION OF THE DRAWING

Figure 4:
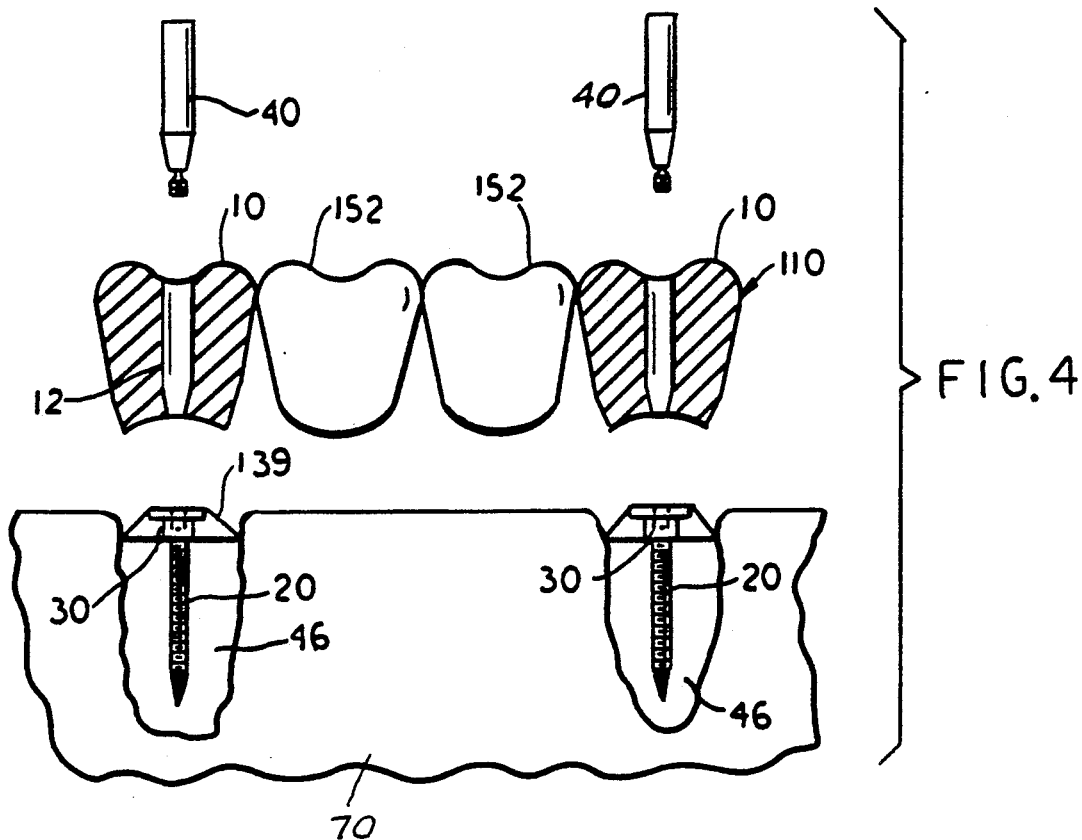
FIG. 4 is an exploded view of a bridge and associated structure to be supported by two posts each in one of the two natural teeth.

Now with more particular reference to the drawing, referring to FIG. 1 through 3, dental post 20 is shown used in combination with natural tooth 46 and jaw bone 70 wherein crown 10 is to be removably supported on natural tooth 46. Super structure 30 may be made as an integral part of dental post 20 and the dental post may be made of a single piece of material.

Dental post 20 is an elongated member having first end 22 and second end 24. The outer periphery of dental post 20 may be threaded or may have closely spaced notches 26.

Super structure 30 has outwardly directed flange 32 which could be integrally connected to cylindrical body 36 and may be supported on filling material 39. The filling material 39 which will extend up to the outer periphery of outwardly directed flange 32 and flat end 34 will form a continuous surface with filling material 39. Threaded bore 35 is formed in cylindrical body 36 which may receive threaded end 44 of retention member 40.

Retention member 40 has elongated hollow cylindrical body 49 extending from first hex end 42 to second end 43. Second end 43 is integrally attached to inwardly and downwardly extending tapered part 45. Tapered part 45 terminates at flat inwardly extending shoulder 48. Reduced size threaded end 44 is joined to flat inwardly extending shoulder 48 by unthreaded part 41 and extends to reduced size threaded end 44 which may be received in threaded bore 35 in superstructure 30. Hollow bore 47 in retention member 40 is hex shaped at its end 42 to receive a wrench.

Crown 10 may be made of metal in accordance with dental techniques familiar to those skilled in the art. Crown 10 has hollow cylindrical bore 12 having cylindrical wall 14 which terminates at its lower end in internal taper 16. Hollow cylindrical bore 12 snugly receives retention member 40. Tapered part 45 on retention member 40 will engage internal taper 16 on crown 10 holding crown 10 down. Concave end 18 of crown 10 rests on filling material 39 and on flat end 34 of super structure 30. Crown 10 may be removed periodically for inspection by the dentist by inserting a hex shaped wrench in first hex end 42 of retention member 40 and loosening retention member 40. Natural tooth 46 may have root canal filling 50 which may be installed by known dental techniques. Concave end 18 may be forced down into engagement with filling material 39 by a wrench inserted into first hex end 42.

Now with reference to the embodiment shown in FIG. 4, an exploded view of bridge 110 is shown using applicant's dental posts 20. Bridge 110 is made up of pontics 152 which may be connected together and fixed to crowns 10 which are similar to crown 10 shown in FIG. 1.

Dental posts 20 are received on natural tooth 46. Retention members 40 extend through hollow cylindrical bores 12 in crowns 10 and reduced size threaded ends 44 of retention member 40 threadably engage super structure 30. Bridge 110 can be removed from time to time by engaging first hex end 42 in retention member 40 with a suitable wrench and unscrewing retention member 40 from super structure 30 and bridge 110 then inspected and replaced.

Figure 5:
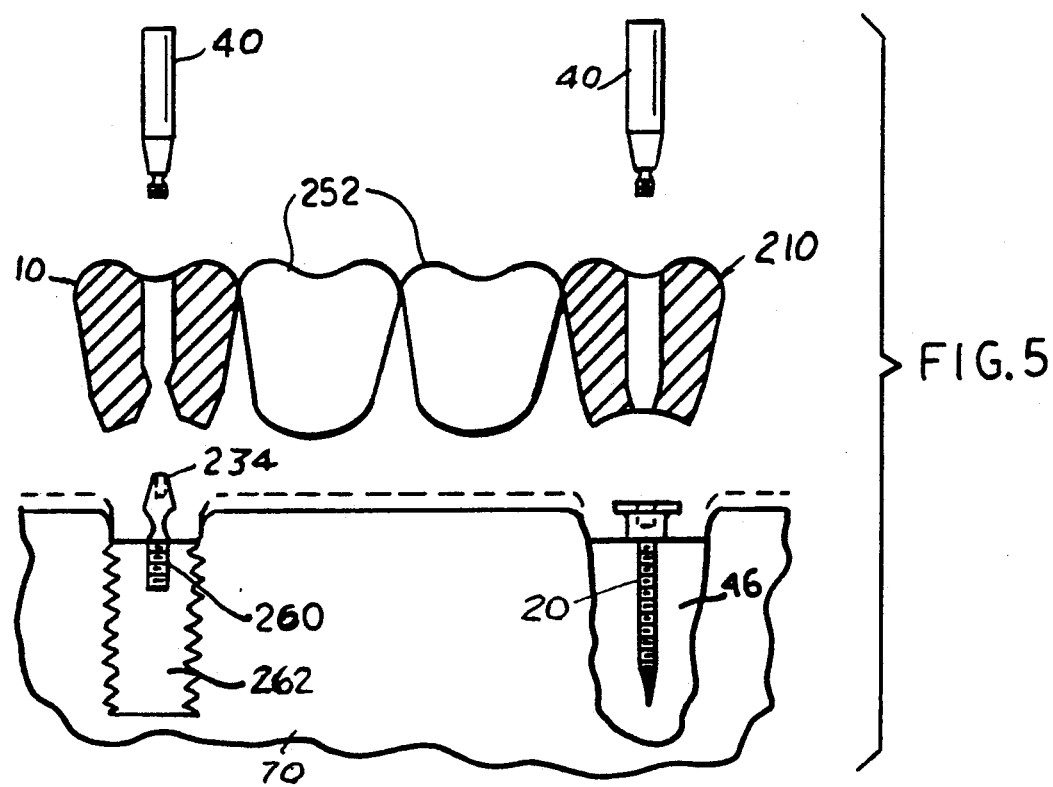
FIG. 5 is an exploded view of a bridge to be supported on one post in a natural tooth and one post in an implant respectively according to the invention.

In the embodiment of the invention shown in FIG. 5, bridge 210 is shown supported on natural tooth 46 and by implant 262. Bridge 210 incorporates pontics 252. One retention member extends through hollow cylindrical bore 12 of each crown 10, as in FIG. 1 and threadably engages super structure 30. The other retention member 40 threadably engages implant fixture screw 260 in implant 262. Bridge 210 can therefore be removed and replaced by removing and replacing retention members 40.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. In combination, a dental post, a prosthesis and a retention member;
   said dental post comprising an elongated cylindrical body having a super structure, a first end, a second end, a threaded bore and an outer periphery having spaced notches;
   said retention member having a hollow cylindrical body part;
   said hollow cylindrical body part of said retention member having a tapered part and a reduced size threaded part;
   said reduced size threaded part being attached to said tapered part;
   said threaded bore of said body of said dental post being adapted to receive said reduced size threaded part of said retention member;
   said prosthesis having a concave end adapted to rest on filling material supported on a natural tooth;
   a hollow cylindrical bore in said prosthesis terminating in a tapered surface adjacent said concave end;
   said hollow cylindrical bore in said prothesis being adapted to receive said retention member;
   said tapered part of said retention member being adapted to engage said tapered surface of said prothesis to pull said prothesis into engagement with said filling material on said natural tooth when said reduced size threaded part of said retention member is tightened into said threaded bore of said dental post.

2. The combination recited in claim 1 wherein an implant is spaced from said natural tooth;
   said prosthesis is a bridge;
   a second retention member is provided for attaching said bridge to said implant whereby said bridge is held to said implant and can be removed.

3. The combination recited in claim 2 wherein said prothesis comprises a plurality of crowns attached together.

4. The combination recited in claim 2 wherein said bridge comprises at least two pontics and connecting means connecting said pontics together.

5. The combination recited in claim 2 wherein said prothesis comprises a first crown and a second crown; and,
   said first crown is attached to said natural tooth and said second crown is attached to said implant.

6. A method of installing a prothesis on a natural tooth comprising;
   providing a dental post having a super structure, an internal threaded bore, a retention member having a hollow cylindrical body having a reduced size threaded end and a tapered surface joining said hollow cylindrical body with said reduced size threaded end and a tool engaging surface on said retention member;
   said method further including said prothesis having a concave end complementary in shape to said hollow cylindrical body and to a surface of said dental post;
   said method further comprises preparing a surface of said natural tooth to receive said prothesis;
   inserting said dental post through said prepared surface into said natural tooth;
   inserting said retention member into said prothesis;
   inserting said reduced size threaded end of said retention member into said threaded bore of said dental post;
   tightening said retention member in said dental post whereby a surface of said dental post engages an internal taper on said prothesis and forces said prothesis into engagement with a filling material on said natural tooth whereby said tool engaging surface is exposed for engagement with said natural tooth to release said retention member from said dental post and said prothesis may be removed from said natural tooth for inspection and replacement.

7. The method of claim 6 further including said super structure of said dental post having an outwardly extending flange;
   applying said filling material to said natural tooth covering said outwardly extending flange before said reduced size threaded end of said retention member is inserted into said threaded bore; and,
   resting said prothesis on said filling material on said dental post.

* * * * *